United States Patent [19]

MacDonald

[11] Patent Number: 4,835,145
[45] Date of Patent: * May 30, 1989

[54] 16,17 ACETALS OF PREGNANE DERIVATIVES AND PHARMACEUTICAL COMPOSITIONS CONTAINING THEM

[75] Inventor: Peter MacDonald, Milan, Italy

[73] Assignee: Sicor Societa' Italiana Corticosteroidi S.p.A., Milan, Italy

[*] Notice: The portion of the term of this patent subsequent to Sep. 22, 2004 has been disclaimed.

[21] Appl. No.: 185

[22] Filed: Jan. 2, 1987

Related U.S. Application Data

[63] Continuation-in-part of Ser. No. 739,131, May 30, 1989, Pat. No. 4,695,625.

[30] Foreign Application Priority Data

Jun. 11, 1984 [IT] Italy ................ 21343 A/84

[51] Int. Cl.⁴ ............ A61K 31/58; C07J 71/00
[52] U.S. Cl. ................ 514/174; 540/63
[58] Field of Search ............ 540/63; 514/174

[56] References Cited

U.S. PATENT DOCUMENTS

| | | |
|---|---|---|
| 3,929,768 | 12/1975 | Brattsand et al. ........ 540/63 |
| 3,983,233 | 9/1976 | Brattsand et al. ........ 540/63 |
| 3,996,359 | 12/1976 | Brattsand et al. ........ 540/63 |
| 4,404,200 | 9/1983 | Thalen et al. ........ 540/63 |
| 4,695,625 | 9/1987 | MacDonald ........ 540/63 |

Primary Examiner—Leonard Schenkman
Assistant Examiner—Joseph A. Liponsky
Attorney, Agent, or Firm—Walter H. Schneider

[57] ABSTRACT

A compound exhibiting anti-inflammatory properties having the formula

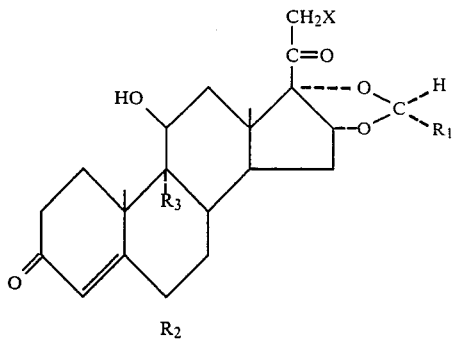

in which X is H, Hal or $CH_3COO-$; $R_1$ is $CH_3(CH_2)_2CH-$; and $R_2$ and $R_3$ are separately H or Hal; and a pharmaceutical composition containing the same.

15 Claims, No Drawings

16,17 ACETALS OF PREGNANE DERIVATIVES AND PHARMACEUTICAL COMPOSITIONS CONTAINING THEM

This application is a continuation-in-part of appl. ser. no. 739,131 filed May 30, 1985, now U.S. Pat. No. 4,695,625.

The present invention relates to 16,17 acetals of pregnane derivatives and to pharamceutical compositions containing them.

The 16,17 acetals of pregnane derivatives according to this invention have the following general formula:

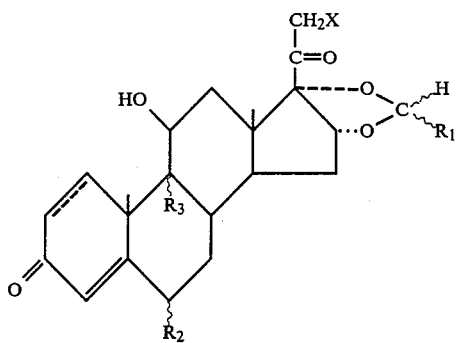

wherein $R_1$ is $CH_3(CH_2)_2CH—$, $R_2$ and $R_3$ are separately selected from H and Hal, and X is H, Hal or $CH_3COO—$. Specifically, the compounds according to this invention are the following:

9α-fluoro-21-chloro-16α,17α-butylidenedioxy-11β-hydroxypregna-4-ene-3,20-dione;

6α-fluoro-16α,17β-butylidenedioxy-11β,21-dihydroxypregna-4-ene-3,20-dione;

9α-fluoro-16α,17α-butylidenedioxy-11β,21-dihydroxypregna-4-ene-3,20-dione;

6α-fluoro-9α-chlor0-16α,17α-butylidenedioxy-11β-hydroxy, 21-acetoxy-pregna-4-ene-3,20-dione.

The compounds of this invention can be prepared by reacting 16,17-acetonides with aldhydes having the formula $R_1CHO$, in which $R_1$ has the meaning given above, in molar ratios ranging from 1:1 to 1:5, preferably from 1:1 to 1:1.1, in aqueous hydrofluoric acid and concentrations ranging from 20 to 90%, preferably from 50 to 70%, at a temperature from −70° to 20° C., the temperature being choosen in order to give the desired epimer ratio.

The product is isolated by simple water dilution, in high purity.

Although working with unitary stoichiometric ratios between the steroidal substrate and the carbonyl compound, the reaction takes place in almost quantitative yields.

Alternatively, instead of hydrofluoric acid, it is possible to use hydrochloric acid. In this case, however, the reaction is less selective in the isomers ratio and the product obtained is less pure.

It should be noted that the acetonide can be replaced by the corresponding diol derivative. Under these conditions the acetal is always produced with an excess of the B epimer, but with a lower selectivity.

Another aspect of the invention, equally important, concerns the conversion of the less active epimer of a 16,17-acetal into the more active epimer. For instance, a mixture of budesonide containing only 30% of the B epimer, subjected to the above mentioned conditions for the preparation of budesonide from the corresponding acetonide, is transformed into budesonide having more than 90% of B epimer. This process is very useful to recover active product from the mother liquors (as deriving from the crystallization) enriched in A epimer. For the epimerization of budesonide like compounds it is sufficient the treatment with hydrofluoric acid alone but, usually, an amount (lower than the stoichiometric one) of the aldehyde (in the instance of budesonide, butyraldehyde) is added in order to avoid any formation of the 16,17-diol.

The following non limiting examples further illustrate the invention. The designation "A epimer" or "B epimer" is made according to U.S. Pat. No. 3,928,326 and the epimer ratio was determined by HPLC using a reversed phase RP-18 column, eluting with 40% acetonitrile.

EXAMPLE 1

50 Grams of desonide (16β-hydroxyprednisolone-16,17-acetonide) and immediately thereafter 12,5 ml of butyraldehyde were added to 500 ml of a 70% hydrofluoric acid solution, at −5° C. The mixture was stirred at 0° C. for one hour and then poured into 5 liters of demineralized water at 0° C. The precipitate was filtered, washed to neutrality with water and dried under vacuum to give 51 g of pure budesonide with an A/B epimer ratio of 9/91.

EXAMPLE 2

The procedure described in Example 1 was repeated, except that the desonide was replaced by other acetonides. The corresponding acetals with butyraldehyde were obtained in almost quantitative yields and with the epimer ratios reported in the following Table I.

TABLE I

| Compound | Starting product | Final product | Ratio A/B epimer |
|---|---|---|---|
| 2a | Desonide 21-acetate | Budesonide 21-acetate | 13/87 |
| 2b | Triamcinolone acetonide | 9α-Fluoro-budesonide | 15/85 |
| 2c | Fluocinolone acetonide | 6α,9α-Difluoro-budesonide | 11/89 |
| 2d | Flunisolide | 6α-Fluoro-budesonide (6α-Fluoro-16α, 17α-butylidenedioxy-11β, 21-dihydroxy-pregna-1,4-diene-3,20-dione) | (Apparently only one epimer) |
| 2e | Flurandrenolide | 6α-Fluoro-16α,17α-butylidenedioxy-11β,21-dihydroxypregna-4-ene-3,20-dione | (Apparently only one epimer) |
| 2f | Alcinonide | 9α-Fluoro-21-chloro-16α,17α-butylidenedioxy-11β-hydroxy-pregna-4-ene-3,20-dione | 12/88 |
| 2g | 9α-Fluoro-16α,17α-iso- | 9α-Fluoro-16α,17α-butylidenedio- | 9/91 |

TABLE I-continued

| Compound | Starting product | Final product | Ratio A/B epimer |
|---|---|---|---|
| | propylidenedioxy-11$\beta$,21-dihydroxy-pregna-4-ene-3,20-dione | xy-11$\beta$,21-dihydroxypregna-4-ene-3,20-dione | |
| 2h | 21-Acetoxy-16$\alpha$,17$\alpha$-isopropylidenedioxy-11$\beta$-hydroxypregna-4-ene-3,20-dione | 21-Acetoxy-16$\alpha$,17$\alpha$-butylidenedioxy-11$\beta$-hydroxypregna-4-ene-3,20-dione | 10/90 |
| 2i | 6$\alpha$-Fluoro-9$\alpha$-chloro-desonide 21-acetate | 6$\alpha$-Fluoro-9$\alpha$-chloro-budesonide 21-acetate | 10/90 |
| 2j | Fluocinonide | 6$\alpha$,9$\alpha$-Difluoro-budesonide 21-acetate | ca. 15/85 |

EXAMPLE 3

The procedure described in Example 1, was repeated, except that the reaction was carried out at $-78°$ (and quenching the reaction after 12 hours at this temperature). Budesonide was obtained (A/B ratio 47/53) together with unreacted desonide (about 40%).

EXAMPLE 4

The procedure described in Example 1 was repeated, substituting butyraldehyde by isobutyraldehyde. 16$\alpha$-Hydroxyprednisolone 16,17-acetal, apparently only one epimer, was obtained.

EXAMPLE 5

Under the same conditions as in Example 1, but using 16$\alpha$-hydroxyprogesterone instead of desonide, budesonide was obtained (A/B ratio 16/84).

EXAMPLE 6

Under the same conditions as in Example 1, but using budesonide (A/B ratio 70/50) instead of desonide, budesonide having A/B ratio of 10/90 was obtained.

EXAMPLE 7

To illustrate the topical anti-inflammatory efficacy of the new compounds according to the present invention, the compounds identified in Table I as 2e, 2f and 2g were compared to the compound of Example 3 of U.S. Pat. No. 4,404,200. The compounds were compared on the basis of their ability to inhibit cotton-pellet induced granulomas (concentration necessary for 50% inhibition, method of Meier, Experientia, 6, 469, 1950). Results appear in the following Table II.

TABLE II

| Compound | Relative Topical Anti-Inflammatory Potency (Budesonide = 1) |
|---|---|
| Ex. 3 USP 4,404,200 | 0.39 |
| 2e | 3.03 |
| 2f | 4.86 |
| 2g | 1.80 |

EXAMPLE 8

Compound 2i of Table I was similarly compared to the compound of Example 22 of U.S. Pat No. 3,983,233. Results appear in the following Table III.

TABLE III

| Compound | Relative Topical Anti-Inflammatory Potency (Budesonide = 1) |
|---|---|
| Ex. 22 USP 3,983,233 | 1.49 |

TABLE III-continued

| Compound | Relative Topical Anti-Inflammatory Potency (Budesonide = 1) |
|---|---|
| 2i | 5.90 |

The present invention also relates to a method for the treatment of inflammatory conditions using a pharmaceutical composition comprising an effective amount of a compound as herein described together with a pharmaceutically acceptable carrier. Pharmaceutical dosage forms are prepared according to procedures well known in the art and, where suitable, the compositions as herein described may contain other active ingredients, e.g., antibiotics.

The following examples illustrate topical formulations prepared in accordance with this invention:

| | |
|---|---|
| (a) Inhalation Aerosol | |
| 9$\alpha$-Fluoro-21-chloro-16$\alpha$,17$\alpha$-butylidenedioxy-11$\beta$-hydroxypregna-4-ene-3,2-dione | 1-10 mg |
| Oleic Acid | 0.5 mg |
| Trichlorofluormethane | 3000 mg |
| Diclorofluormethane | 7500 mg |
| (b) Lotion | |
| 6$\alpha$-Fluoro-16$\alpha$,17$\alpha$-butylidenedioxy-11$\beta$,21-dihydroxypregna-4-ene-3,20-dione (Compound 2e) | 0.05-5.0 mg |
| Ethyl alcohol | 400 mg |
| Polyethyleneglycol 400 | 300 mg |
| Hydroxypropyl cellulose | 5 mg |
| Propylene glycol | 300 mg |
| (c) Glycol Ointment | |
| 9$\alpha$-Fluoro-16$\alpha$,17$\alpha$-butylidenedioxy-11$\beta$,21-dihydroxypregna-4-ene-3,20-dione (Compound 2g) | 0.05-5.0 mg |
| Hexylene glycol | 100 mg |
| Propylene glycol monstearate | 20 mg |
| White wax | 60 mg |
| White petrolatum | 880 mg |
| (d) Cream | |
| 6$\alpha$-Fluor-9$\alpha$-chloro-16$\alpha$,17$\alpha$-butylidenedioxy-11$\beta$-hydroxy, 21-acetoxy-pregna-4-ene-dione (Compound 2i) | 10-100 mg |
| Propylene glycol | 47.5 mg |
| Glyceryl monostearate self-emulsifying | 1.5 mg |
| Glyceryl monostearate | 10.5 mg |
| Cetostearylic alcohol | 8.0 mg. |
| White beeswax | 1.25 mg |
| Chlorocresol (4-chloro-3-methylphenol) | 0.075 mg |
| Sodium citrate | 0.05 mg |
| Citric acid | 0.05 mg |
| Purified water q.s. to | 100 mg |

I claim:

1. A compound according to the formula

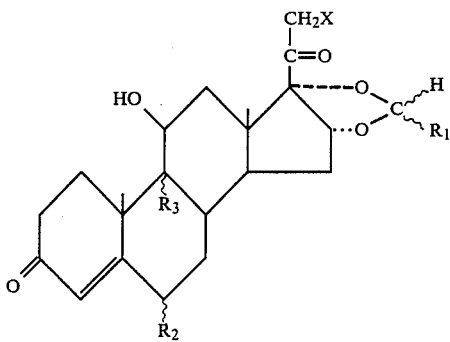

in which X is H, Hal or CH₃COO-; R₁ is CU₃(CH₂)₂CH-; and R₂ and R₃ are separately H or Hal.

2. A pharmaceutical composition having anti-inflammatory properties comprising as the active ingredient an effective amount of a compound according to claim 1 together with a pharmaceutically acceptable carrier.

3. A method of treating inflammatory conditions which comprises administering to a patent an anti-inflammatory effective amount of a composition according to claim 2.

4. 9α-Fluoro-21-chloro-16α,17β-butylidenedioxy-11β-hydroxypregna-4-ene-3,20-dione.

5. A pharmaceutical composition having antiinflammatory properties comprising as the active ingredient an effective amount of the compound according to claim 4 together with a pharmaceutically acceptable carrier.

6. A method of treating inflammatory conditions which comprises administering to a patient an anti-inflammatory effective amount of a composition according to claim 5.

7. 6α-Fluoro-16α,17β-butylidenedioxy-11α,21-dihydroxypregna-4-ene-3,20-dione.

8. A pharmaceutical composition having antiinflammatory properties comprising as the active ingredient an effective amount to the compound according to claim 7 together with a pharmaceutically acceptable carrier.

9. A method of treating inflammatory conditions which comprises administering to a patient an anti-inflammatory effective amount of a composition according to claim 8.

10. 9α-fluoro-16α,17α-butylidenedioxy-11β,21-dihydroxypregna-4-ene-3,20-dione.

11. A pharmaceutical composition having anti-inflammatory properties comprising as the active ingredient an effective amount of the compound according to claim 10 together with a pharmaceutically acceptable carrier.

12. A method of treating inflammatory conditions which comprises administering to a patient an anti-inflammatory effective amount of a composition according to claim 11.

13. 6α-Fluoro-9α-chloro-16α,17β-butylidenedioxy-11β-hydroxy, 21-acetoxy-pregna-4-ene-3,20-dione.

14. A pharmaceutical composition having antiinflammatory properties comprising as the active ingredient an effective amount of the compound according to claim 13 together with a pharmaceutically acceptable carrier.

15. A method of treating inflammatory conditions which comprises administering to a patient an anti-inflammatory effective amount of a composition according to claim 14.

* * * * *